United States Patent
Engh et al.

(10) Patent No.: US 6,180,138 B1
(45) Date of Patent: *Jan. 30, 2001

(54) PROCESS FOR PREPARING SOLID FORMULATIONS OF LIPID-REGULATING AGENTS WITH ENHANCED DISSOLUTION AND ABSORPTION

(75) Inventors: Kevin R. Engh, Mundelein; Yihong Qiu, Gurnee; Thomas L. Reiland, Gages Lake, all of IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/239,889

(22) Filed: Jan. 29, 1999

(51) Int. Cl.⁷ ................. A61K 9/20; A61K 9/48
(52) U.S. Cl. ............ 424/451; 424/452; 424/456; 424/464; 424/465; 514/772.3; 514/777; 514/778

(58) Field of Search .................. 424/451, 452, 424/456, 464, 465

(56) References Cited

U.S. PATENT DOCUMENTS

| | | | |
|---|---|---|---|
| 4,058,552 | 11/1977 | Mieville | 560/52 |
| 4,739,101 | 4/1988 | Bourgogne et al. | 560/61 |
| 4,800,079 | 1/1989 | Boyer | 424/482 |
| 4,895,726 | 1/1990 | Curtet et al. | 424/456 |
| 4,961,890 | 10/1990 | Boyer | 264/113 |
| 5,645,856 | 7/1997 | Lacy et al. | 424/455 |

FOREIGN PATENT DOCUMENTS

| | | |
|---|---|---|
| 0793958 | 2/1997 | (EP) . |
| 8201649 | 5/1982 | (WO) . |

*Primary Examiner*—James M. Spear
(74) *Attorney, Agent, or Firm*—Dugal S. Sickert

(57) ABSTRACT

A process for the preparation of solid formulations of a lipid-regulating agent having enhanced dissolution and absorption characteristics, in which a micronized mixture of the said lipid-regulating agent, and optionally one or more excipients, is suspended in a surfactant solution, dried and optionally granulated, and optionally converted to a finished dosage form.

16 Claims, 1 Drawing Sheet

PROCESS FOR PREPARING SOLID FORMULATIONS OF LIPID-REGULATING AGENTS WITH ENHANCED DISSOLUTION AND ABSORPTION

FIELD OF THE INVENTION

The present invention relates to a novel process for preparing solid formulations of lipid-regulating agents with enhanced dissolution and absorption characteristics.

BACKGROUND OF THE INVENTION

2-[4-(4-chlorobenzoyl)phenoxy]-2-methyl-propanoic acid, 1-methylethylester, also known as fenofibrate, is representative of a broad class of compounds having pharmaceutical utility as lipid-regulating agents. More specifically, this compound is part of a lipid-regulating agent class of compounds commonly known as fibrates, and is disclosed in U.S. Patent No. 4,058,552.

Fenofibrate has been prepared in several different formulations, c.f., U.S. Pat. No. 4,800,079 and U.S. Pat. No. 4,895,726. U.S. Pat. No. 4,895,726 discloses a co-micronized formulation of fenofibrate and a solid surfactant.

U.S. Pat. No. 4,961,890 discloses a process for preparing a controlled release formulation containing fenofibrate in an intermediate layer in the form of crystalline microparticles included within pores of an inert matrix. The formulation is prepared by a process involving the sequential steps of dampening said inert core with a solution based on said binder, then projecting said fenofibrate microparticles in a single layer onto said dampened core, and thereafter drying, before said solution based on said binder dissolves said fenofibrate microparticles, and repeating said three steps in sequence until said intermediate layer is formed.

European Patent Application No. EP0793958A2 discloses a process for producing a fenofibrate solid dosage form utilizing fenofibrate, a surface active agent and polyvinyl pyrrolidone in which the fenofibrate particles are mixed with a polyvinyl pyrrolidone solution. The thus obtained mixture is granulated with an aqueous solution of one or more surface active agents, and the granulate thus produced is dried.

PCT Publication No. WO82/01649 discloses a fenofibrate formulation having granules that are comprised of a neutral core that is a mixture of saccharose and starch. The neutral core is covered with a first layer of fenofibrate, admixed with an excipient and with a second microporous outer layer of an edible polymer.

U.S. Pat. No. 5,645,856 discloses the use of a carrier for hydrophobic drugs, including fenofibrate, and pharmaceutical compositions based thereon. The carrier comprises a digestible oil and a pharmaceutically-acceptable surfactant component for dispersing the oil in vivo upon administration of the carrier, which comprises a hydrophilic surfactant, said surfactant component being such as not to substantially inhibit the in vivo lipolysis of the digestible oil.

The prior art processes obtained small particles of fenofibrate by the use of co-micronization steps of the drug with a surfactant. These resulting formulations may not have the maximized dissolution rate.

It is an object of the present invention to provide rapid dissolution of lipid-regulating agents, more preferably fenofibrate, having enhanced dissolution and absorption characteristics than those particles of such agents prepared by prior art techniques.

SUMMARY OF THE INVENTION

The present invention is directed to a process for preparing a solid formulation of a lipid-regulating agent with enhanced dissolution and absorption characteristics.

In this process, the lipid-regulating agent is coated with a surfactant by drying a suspension of said agent in a solution of said surfactant. This results in a formulation having enhanced wetting, dissolution and bioavailability characteristics, when compared to a formulation prepared by prior art techniques.

More particularly, the present process comprises the steps of premixing the lipid-regulating agent with an excipient, micronizing the powdered mixture, suspending the micronized powdered mixture in a surfactant solution, drying the mixture, wet or dry granulating the mixture (optionally with other excipients), and optionally forming a finished oral dosage form of the resulting formulation.

The finished oral dosage form may be prepared by techniques well-known to those skilled in the art by sizing the mixture, dry blending the resultant particles with excipients into the finished oral dosage form, preferably as a tablet or capsule.

The formulation thus produced may be administered directly, diluted into an appropriate vehicle for administration, encapsulated into hard gelatin shells or capsules for administration, or administered by other means obvious to those skilled in the art.

DETAILED DESCRIPTION OF THE INVENTION

Figure 1:
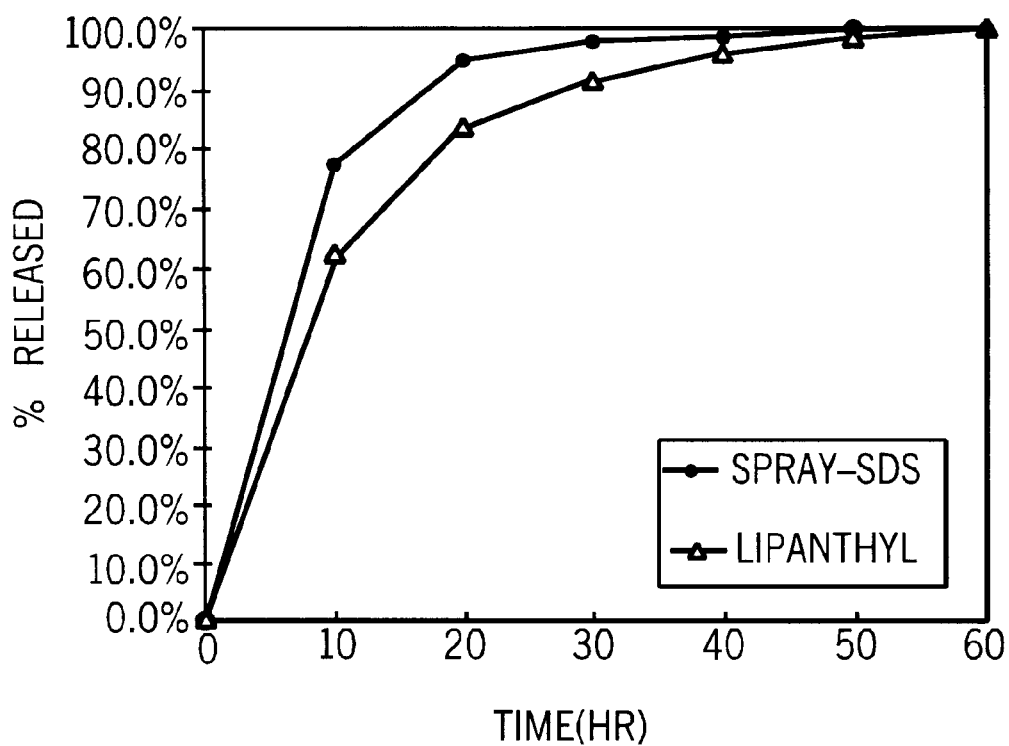
FIG. 1 is a graph showing the respective dissolution characteristics of representative compositions prepared by the process of the present invention and compositions prepared by techniques of the prior art.

The bulk lipid-regulating agent can be prepared by any available method, as for example the compound fenofibrate may be prepared by the procedure disclosed in U.S. Pat. No. 4,658,552, or the procedure disclosed in U.S. Pat. No. 4,739,101, both herein incorporated by reference.

The lipid-regulating agent is then premixed with lactose or another suitable excipient, such as, for example, sucrose or mannitol, in amounts ranging from five parts by weight excipient to 95 parts by weight lipid-regulating agent, to 15 parts by weight excipient to 85 parts by weight lipid-regulating agent.

The mixture is then micronized using a jet mill, as for example, a Model 60JET-OMIZER device available from Fluid Energy Aljet, or other suitable means.

The milled particle mixture is then suspended in a surfactant solution, such as, for example, sodium lauryl sulfate, with mixing, stirring or shaking. Other suitable surfactants may include all pharmaceutally acceptable anionic, cationic, ampholytic, nonionic surfactants, such as poloxamer polyols, d-alpha tocopheryl polyethylene glycol succinate and polyoxyl 40 stearate.

The surfactant solution may also contain the presence or absence of an electrolyte, such as, for example, NaCl, in an amount ranging from 4% to 25% of the total formulation by weight. The amount of lipid-regulating agent mixture and surfactant is in the range of about ten parts by weight agent to about one part by weight surfactant, to about twenty parts by weight agent to about one part by weight surfactant.

Other pharmaceutically-acceptable excipients may be added to the formulation prior to forming the desired final product. Suitable excipients include, for example, lactose, starch, polyvinyl pyrrolidone and magnesium stearate.

The resulting suspension is then dried by well-known solvent evaporation techniques, such as, for example, spray drying, spinning disk drying mechanisms, fluid bed, or evaporation, under reduced pressure. A preferred means of spray drying utilizes a Buchi mini-spray dryer, model No. B-191. The resultant material may be sized, if necessary, and optionally formulated into a finished oral dosage form, such as, for example, a tablet or capsule by conventional techniques such as direct compression or other means.

The invention will be understood more clearly from the following non-limiting representative examples:

EXAMPLE 1

A. 12g milled fenofibrate:lactose (95:5) particles were added to sodium lauryl sulfate (SDS) aqueous solution (1.29/250 mL) with mixing. The resulting suspension was shaken well, sonicated, and made ready for spray drying. Final composition: fenofibrate=86.4%; lactose=4.5%; SDS=9.1%.

B. In a manner analogous to Example 1A, 15 g milled fenofibrate:lactose (85:15) particles were added to a SDS aqueous solution (0.9 g/250 mL), shaken well to form a suspension, sonicated, and made ready for spray drying. Final Composition: fenofibrate=80.2%; lactose=14.1%; SDS=5.7%

C. In a manner analogous to Example 1A, 30 g milled fenofibrate:lactose (90:10) particles were added to a SDS aqueous solution (0.9 g/250 mL) along with 3 g NaCl. The mixture was shaken well to form a suspension, sonicated, and made ready for spray drying. Final composition: fenofibrate=77.58%; lactose=8.62%; SDS=5.2%; NaCl=8.6%.

D. The mixtures from Examples 1A and 1B were spray dried using a Buchi Mini Spray Dryer B-191, under the following spray drying conditions:

| | |
|---|---|
| Heating inlet temperature = | 100° C. |
| Outlet = | 38° C. |
| Aspirator = | 100% |
| Pump = | 30% (~9 mL/min) |
| $N_2$ (air) flow = | 600 (L/hr) |

EXAMPLE 2

Representative compositions prepared by the process of the present invention were evaluated in a dissolution test against a commercial formulation of fenofibrate and a reference formulation consisting of a physical mixture of SDS and micronized fenofibrate. The results are set forth in FIG. 1 and demonstrate the improved dissolution characteristics of the formulation prepared by the process of the present invention.

What is claimed is:

1. A process for preparing a solid formulation of a lipid-regulating agent, wherein such lipid-regulating agent is a fibrate, comprising suspending said lipid-regulating agent with a surfactant solution in the presence or absence of an electrolyte; drying the mixture; granulating the mixture optionally in the presence of one or more excipients; and optionally forming a finished dosage form.

2. A composition prepared by the process of claim 1.

3. A process of claim wherein the fibrate is fenofibrate.

4. A process of claim 3 wherein the mixture is dried by a method selected from the group consisting of spray drying, fluid bed, spinning disk drying and evaporation under reduced pressure.

5. A process of claim 4 wherein the mixture is dried by spray drying.

6. A process of claim 3 wherein the surfactant is sodium lauryl sulfate.

7. A process of claim 5 where the surfactant coexists with an electrolyte.

8. A process of claim 7 wherein the electrolyte is NaCl.

9. A process of claim 8 further comprising adding one or more excipients to the granulated mixture.

10. A process of claim 9 wherein the excipient is at least one pharmaceutically acceptable excipient selected from the group consisting of lactose, starch, polyvinyl pyrrolidone and magnesium stearate.

11. A process of claim 3 further comprising forming a finished dosage form.

12. A process of claim 11 wherein the finished dosage form is a capsule.

13. A process of claim 11 wherein the finished dosage form is a tablet.

14. A method of treating hyperlipidemia comprising the administration of a formulation prepared by the process of claim 1 to a patient.

15. A method of claim 14 wherein the fibrate is fenofibrate.

16. A composition prepared by the process of claim 3.

* * * * *

UNITED STATES PATENT AND TRADEMARK OFFICE
CERTIFICATE OF CORRECTION

PATENT NO. : 6,180,138 B1
DATED : January 30, 2001
INVENTOR(S) : Kevin R. Engh, et al.

Page 1 of 1

It is certified that error appears in the above-identified patent and that said Letters Patent is hereby corrected as shown below:

Column 2,
Line 57, please delete "include all pharmaceutally acceptable" and insert -- include all pharmaceutically acceptable --.

Column 3,
Line 26, please delete "a SDS" and insert -- an SDS --.
Line 32, please delete "a SDS" and insert -- an SDS --.

Column 4, claim 3,
Line 1, please delete "claim wherein" and insert -- claim 1 wherein --.

Signed and Sealed this

Twenty-third Day of October, 2001

Attest:

Attesting Officer

NICHOLAS P. GODICI
Acting Director of the United States Patent and Trademark Office

UNITED STATES PATENT AND TRADEMARK OFFICE
CERTIFICATE OF CORRECTION

PATENT NO. : 6,180,138 B1
DATED : January 30, 2001
INVENTOR(S) : Kevin R. Engh, et al.

It is certified that error appears in the above-identified patent and that said Letters Patent is hereby corrected as shown below:

Column 4,
Line 18, "A process of claim wherein the fibrate is fenofibrate." replace with -- A process of claim 1 wherein the fibrate is fenofibrate --.

Signed and Sealed this

Ninth Day of July, 2002

Attest:

Attesting Officer

JAMES E. ROGAN
Director of the United States Patent and Trademark Office